3 Sheets—Sheet 1.

I. L. PULVERMACHER.

ELECTRO-GALVANIC CHAINS, BANDS, &c.

No. 7,209. Reissued July 4, 1876.

Witnesses:
Donn P. Twitchell
Will H. Dodge

Inventor:
I. L. Pulvermacher,
by Dodge & Son
Attys.

N. PETERS, PHOTO-LITHOGRAPHER, WASHINGTON, D. C.

I. L. PULVERMACHER.

ELECTRO-GALVANIC CHAINS, BANDS, &c.

No. 7,209. Reissued July 4, 1876.

Witnesses:
Dunn P. Tortchell
Will H. Dodge

Inventor:
I. L. Pulvermacher,
by Dodge & Son
Attys.

N. PETERS, PHOTO-LITHOGRAPHER, WASHINGTON, D. C.

I. L. PULVERMACHER.

ELECTRO-GALVANIC CHAINS, BANDS, &c.

No. 7,209. Reissued July 4, 1876.

Witnesses:
Donn P. Twitchell.
Will M. Dodge.

Inventor:
I. L. Pulvermacher.
by Dodgerson
Attys.

N. PETERS, PHOTO-LITHOGRAPHER, WASHINGTON, D. C.

UNITED STATES PATENT OFFICE.

ISAAC LOUIS PULVERMACHER, OF LONDON, ENGLAND, ASSIGNOR TO JOHN E. HETHERINGTON, OF CINNCINNATI, OHIO.

IMPROVEMENT IN ELECTRO-GALVANIC CHAINS, BANDS, &c.

Specification forming part of Letters Patent No. 120,772, dated November 7, 1871; reissue No. 7,209, dated July 4, 1876; application filed April 28, 1876.

DIVISION C.

*To all whom it may concern:*

Be it known that I, ISAAC LOUIS PULVERMACHER, of London, England, have invented certain new and useful Improvements in Electro-Galvanic Chains, Bands, &c.; and I do hereby declare that the following is a full, clear, and exact description thereof, reference being had to the accompanying drawings, making part of this specification, and to the letters of reference marked thereon—like letters indicating like parts wherever they occur.

To enable others skilled in the art to construct and use my invention, I will proceed to describe it.

The objects of my invention are to construct plates of copper and zinc, or platinum and zinc, in such a manner that they shall be held and kept in position by means of ribbons, cords, or rods, and thus establish a voltaic chain or pile of great power in a small compass, and so arranged that the zinc plates, when worn out, can be replaced by new ones with facility; also, in the employment of insoluble salts—such as bisulphate of mercury, or chloride of silver—and in apparatus for producing intermittent electrical currents.

Figure 1:
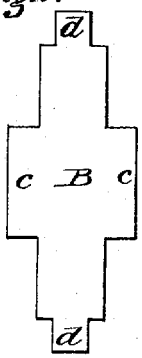
Figure 2:
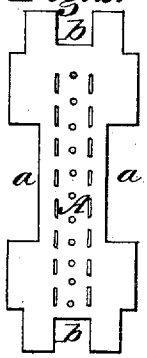
Figure 3:
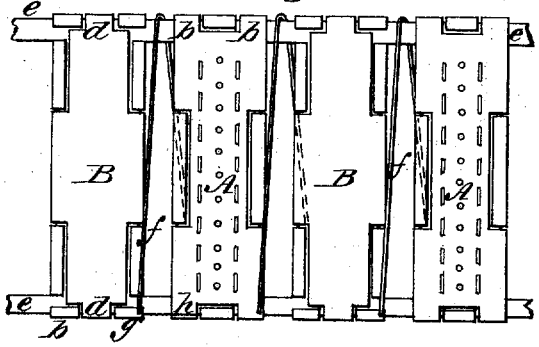
Figure 4:
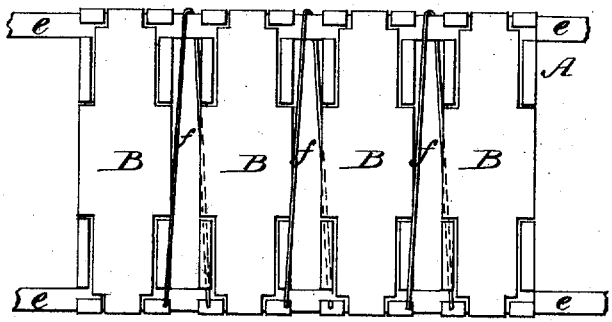

The first part of my invention is represented in Figures 1, 2, 3, and 4 of the accompanying drawings; and consists in forming elements, and in combining the same into a voltaic chain or pile, by making the copper plate A with notches or recesses *a a b b* in its sides and ends, and in forming the zinc plates B with corresponding projections *c c d d* to fit therein without touching the copper plate, the projections on the ends of both of the plates being bent over to gripe and hold a ribbon or tape, *e*, between them, as clearly shown in Figs. 3 and 4, to obtain thereby a mutual fixation, without metallic contact between the negative and positive metal.

By attaching a number of these elements together to the same ribbon a voltaic chain or pile of any length may be made. I solder one end of a wire, *f*, shaped like a hair-pin, to the zinc plate at one corner, *g*, and carry it to, and bend it over, the opposite end, between two elements, and then down to the corner *h* of the copper plate of the next element, and solder it thereto.

Figure 5:
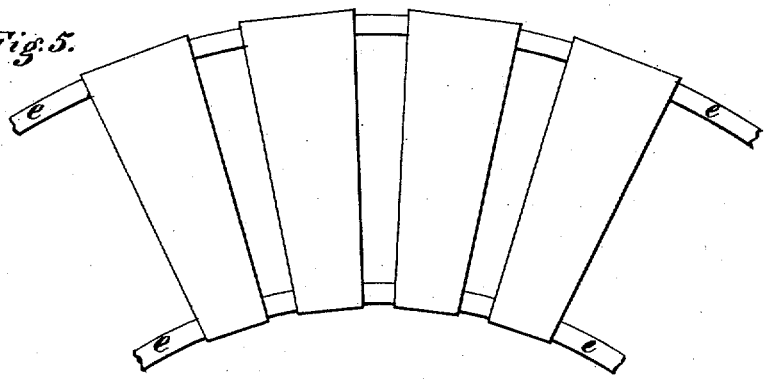
Figure 6:
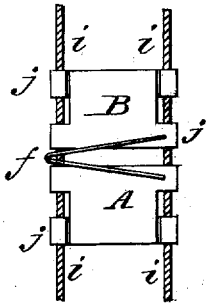

In some cases these plates may be made of a conical shape; and I arrange them upon tapes or ribbons *e e*, to form a fan-shape, a concentric, or a helical battery, the narrow ends being toward the center, as represented in Fig. 5. Sometimes I cut the plates in such a manner that two projections are formed at one end only, as represented in Fig. 6. In that case I turn each projection over upon itself, and form an eye, *j*, by which they may be strung upon an insulated cord, wire, or stem, *i*. The free end *k* of the plate may, or may not, be bent over to hold its neighbor. In some cases I force gutta-percha through perforations or holes in one or both of the plates of each element, to form pins or studs, to keep them apart.

Figure 7:
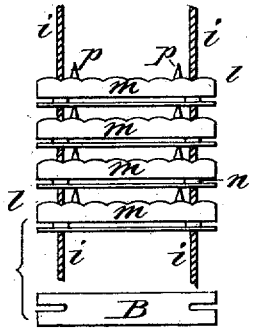
Figure 8:
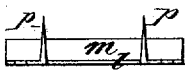

Another part of my invention consists in threading-plates of various shapes, forming the elements upon cords or rods, as shown in Fig. 7. The upper copper plates *l*, in some cases, have their sides or borders *m m* turned at right angles, the zinc plates being flat, and not turned at all. The two plates of two adjoining elements are kept apart by a washer, *n*, or insulating threads of such a thickness that only a small space is left between the zinc and copper plates, to hold a film of exciting-liquid between them, to form a source or means of exciting a current; and, in order to form a voltaic pile, I make on the copper plates projections or spikes *p*, tapered or not, which, when the elements are threaded upon the cords or rods, keep the elements apart by resting against the zinc plates of the adjoining element, and hold them a sufficient distance apart, so that no exciting-liquid will remain in the spaces between one element and the other. The projections or spikes *p* may be composed of portions of the plates slit and turned up from the central part, as in Figs. 7 and 8, or from the edges.

Figure 9:
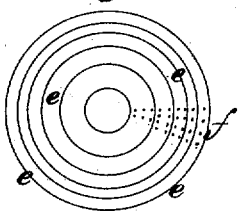
Figure 10:
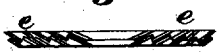

The next part of my invention consists in making circular batteries from very thin sheets of metal, as represented in Figs. 9 and 10. The elements are formed of washers or rings *e e* of different diameters, but each of them is of the same superficial active surface. I place a fabric between the two plates forming each element, and make the battery up to any given size by sewing, as represented by the dots at *f f*. I attach a number of these elements to a water-proof material, and establish contact between the different elements by the outer washer—say, zinc—resting upon the copper of the next element, and so on, to the central washer, which would be of copper. The washers or rings may be sunken toward the center, so that each of them is of concave form. In this manner one rests upon the other, a fabric being laid between to insulate the layers, and to form a means of attachment by sewing or otherwise. In some cases the washers are perforated, to facilitate the exciting-liquid passing into and between the elements with freedom.

Another part of my invention consists in employing negative plates of open-worked form, as described hereafter, so as to form constant elements by means of insoluble metallic salts, capable of electrolysis, and of depolarizing action on the negative part of the element, such as sulphate of lead, bisulphate of mercury, or chloride of silver. The plates may be made in a variety of forms. In some cases I make the elements of open-worked plates in the form of cylinders, or of wire formed into cylinders, and into the inner cylinder of negative metal I put a plug or core of one or other of the insoluble salts before described, but which is enveloped with a porous material. I prevent metallic contact between the negative and positive metals by thread wound spirally upon the wire cylinder, or by thread being laced through holes in the cylinder, if made of plates.

The openings between the wires, or those formed in the cylindrical plate, serve for the fluid to pass through, damp the salt, and excite the element. When the core of salt has lost its properties it can be pushed out and a fresh one inserted.

Figure 11:
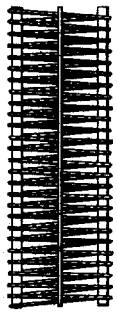

In Fig. 11 I have shown a plate, composed of wire-work, wound upon two uprights or stems. This plate may be shaped into a cylinder, the insulating medium being formed of thread wound spirally upon the wire.

Figure 12:
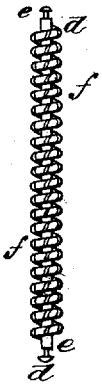
Figure 13:
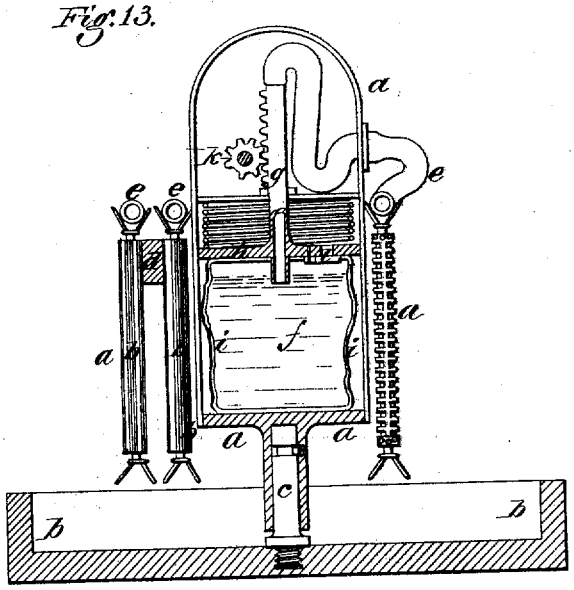
Figure 14:
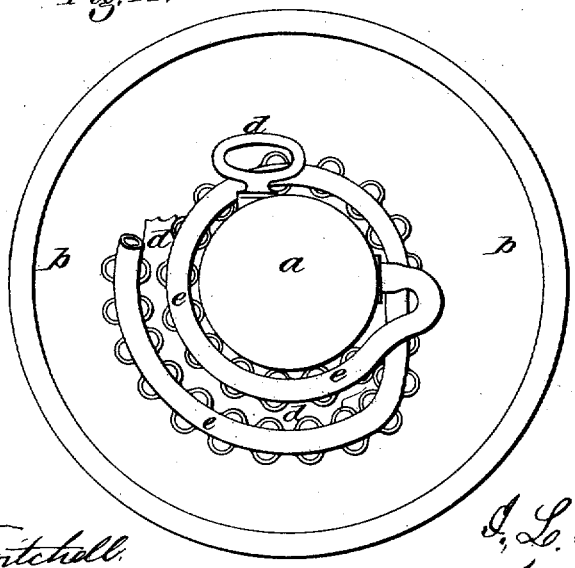

If rods are used as side pieces of the plates or elements they can be formed with annular notches near their ends, (as seen in Fig. 12,) into which perforated end pieces may be forced; or pieces of conductible wire or a narrow strip may be twisted into the notches. After the chains are made up, it is necessary to supply them with the exciting-liquid; and for this purpose the device represented in section in Fig. 13, and in plan in Fig. 14, is admirably adapted. In forming this device I use a circular box or vessel, *a*, of an insulating material, and mount it upon a tray, *b*, so that it may turn freely upon its stem *c*, the outside of the vessel *a* being provided with a strap or length of water-proof fabric, *d*, which has one end loose, so that it may occupy the space between each turn of the chain as it is wound spirally upon the vessel, the thickness of the strap *d* being such that each layer or winding of the chain is kept apart when rolled on. I secure the loose ends of the strap and chain by a hook or other device to hold it firmly thereon. I then take the flexible tube *e*, which is in connection with the reservoir *f*, and lay it in the forks of the chain-wires, the slits in the tube being arranged to come directly over the center of each element or link; and I cause the liquid to run into the tube *g* by pressure of the spring-plate *h*, acting upon the surface of the liquid in the box or vessel *a*. The inside of the vessel may be furnished with a flexible bag, *i*, for holding the liquid, or the vessel itself may form the reservoir. In this case I prefer to use a cup-shaped plunger to act upon the liquid. When the top plate of the bag or the plunger has been forced to the bottom of the reservoir, I draw it up again by turning the key or thumb-screw *j*, so that the pinion *k* acts upon the teeth of the central rod *g*, and lifts it and the plunger.

The reservoir can be kept charged, and the plunger retained in any posion, by fitting a pin in the key, spindle, or other part of the mechanism. The liquid is admitted to the reservoir by passing through the valve *l* in the plate, which opens downward. The elements or links of the chain receiving thus the exciting-liquid will continue to act so long as the automatic supply from the reservoir lasts, and the consumed liquid will drop down and accumulate in the bottom of the tray. The current will remain constant as long as the supply of the exciting-liquid remains uniform. Each pole of these chain-batteries is to be connected to the conducting-wires, by which the electricity is to be conveyed to the place where it has to be applied.

Having thus described my invention, what I claim is—

1. The plates A and B, constructed substantially as described, for forming the elements of a galvanic electric belt or chain.

2. The combination of the plates A and B with the ribbons or cords *e* or *i*, substantially as shown and described, for the formation of a galvano-electric belt or chain.

3. A galvano-electric apparatus, constructed as shown in Figs. 9, 10, 11, and 12, as herein described.

4. The apparatus herein shown and decribed for charging the bands, chains, garments, or articles of dress, as set forth.

5. In combination with a galvano-electric belt or chain, the employment of insoluble salts or chemicals applied thereto, substantiolly as described.

ISAAC LOUIS PULVERMACHER.

Witnesses:

E. N. DANIEL,
166 *Fleet Street, London.*

J. S. ROBINS,
2 *Waterloo Place, Pall Mall, London.*